United States Patent [19]

Zappia et al.

[11] Patent Number: 4,772,463

[45] Date of Patent: Sep. 20, 1988

[54] MACROMOLECULAR CDP-CHOLINE DERIVATIVES, PROCESS FOR THEIR PREPARATION AND PHARMACEUTICAL COMPOSITIONS CONTAINING THEM

[76] Inventors: Vincenzo Zappia, Via San Giacomo Dei Capri, 109/A Napoli; Mario De Rosa, Via Nicolardi, 188 Napoli, both of Italy

[21] Appl. No.: 913,841

[22] Filed: Sep. 30, 1986

[30] Foreign Application Priority Data

Oct. 1, 1985 [IT] Italy ................... 22327 A/85

[51] Int. Cl.$^4$ ............................................. A61K 31/74
[52] U.S. Cl. .......................................... 424/78; 424/81; 525/375; 525/383; 525/384; 525/329.6; 525/329.7; 526/263
[58] Field of Search ............... 526/312, 263; 525/375, 525/383, 384, 329.6, 329.7; 424/78, 81

[56] References Cited

PUBLICATIONS

Chem. Abstracts, vol. 105, entry 61003m.
Chem. Abstracts, vol. 98, entry 73157q.

*Primary Examiner*—Joseph L. Schofer
*Assistant Examiner*—Peter F. Kulkosky

[57] ABSTRACT

CDP-choline derivatives with macromolecules containing carboxy groups, such as polyacrylates, polymethacrylates, polyglutamates, polyaspartates and polymaleates, or copolymers of acrylic acid and methacrylic acid with methyl acrylate, methyl methacrylate or acrylamide.

The polymeric derivatives of the invention gradually release CDP-choline, due to the action of enzymes present in the organism, thus exerting also a protective effect on the CDP-choline molecule.

10 Claims, No Drawings

MACROMOLECULAR CDP-CHOLINE DERIVATIVES, PROCESS FOR THEIR PREPARATION AND PHARMACEUTICAL COMPOSITIONS CONTAINING THEM

The present invention relates to macromolecular CDP-choline derivatives obtained by covalent binding on macromolecular matrices having carboxy groups, processes for the preparation thereof and pharmaceutical compositions containing them.

CDP-choline represents the "active" form of choline and it is a key intermediate in the choline phospholipid biosynthesis (Kennedy E. P. in "Novel Biochemical Pharmacological and Clinical Aspects of CDP-choline", Zappia V. et al., eds. Elsevier N.Y., 3, 1985).

CDP-choline is on its turn biosynthesized from P-choline and CTP by means of the choline-phosphate-cytidinetransferase enzyme, isolated from the microsomial fraction.

The formation of CDP-choline represents the slowest step, thus limiting the whole phospholipid methabolic pathway (Vance D. E. et al., TIBS, 4, 145, 1979): the cellular concentrations of said metabolite play therefore a critical role in the regulation of the phospholipid biosynthesis.

As a consequence of its biochemical roles, the main pharmacological use and prescription of CDP-choline lays in a series of impairments of the Central Nervous System, wherein the structural and functional integrity of the phospholipidic membranes is critical.

The pharmacological activity of the molecule has been shown under different critical conditions such as cerebral apoplexy, different kinds of cerebrovasculopathies, Parkinson's disease, cranial traumathology and consequences thereof (in "Novel Biochemical, Pharmacological and Clinical Aspects of CDP-choline", Zappia et al., eds. Elsevier N.Y., 285, 1985).

The biochemical background underlying such a kind of pharmacology envisaging the use of a molecule deriving from the cytoplasmatic biosynthesis as a drug, is based on the hypothesis that administration of remarkable amounts of said precursor of phospholipids contributes to the re-synthesis and to the repair of the damaged cerebral membranes (Alberghina et al., J. Neuroscience Res., 6, 421, 1981; Alberghina et al., J. Neuroscience Res., 6, 719, 1981; Trovarelli G. et al., Neurochem. Res. 6, 821, 1981). It has been moreover shown that a series of complex biochemical effects of regulatory type, not directly due to the biosynthesis of choline lipids, play an important role in the definition of the therapeutic properties of CDP-choline (Martinet M. et al., Biochem. Pharmacol. 30, 53, 1981; Shibuya M. et al., J. Pharmacol., 31, 47, 1981; Faryna De Raveglia I et al., Neurochem. Res. 7, 37, 1982; Algate D. R. et al., Arzneimittel Forshung Drug. Res., 33, (II), 1022, 1983; Braso M. A. e al., Arzneimittel Forshung Drug. Res., 33, (II), 1043, 1983).

Pharmacodynamics stury at molecular level, carried out using ($5$-$^3$H; Met-$^{14}$C)CDP-choline on different experimental models such as isolated and perfused rat liver, the rat (De Rosa M. et al., in "Novel Biochemical, Pharmacological and Clinical Aspects of CDP-choline", Zappia et al., eds. Elsevier N.Y., 139, 1985) and cultured cerebral cells (Vecchini A. et al., Neurochem. Res. 8, 333, 1983), show that the molecule is actively metabolized. The choline and cytosine components of the drug are found in the lecithine fraction and in the nucleic acids, respectively.

The pharmacodynamic experimentation, carried out on the doubly labelled molecule, shows that the administrations by the intravenous and oral routes are generally comparable as far as the drug bioavailability and the amount of the excretory phenomena of the structural labelled components are concerned, whereas significant differences are noticed in the evolution of the pharmacodynamic pattern and in the nature of the labelled molecular species.

CDP-choline is mainly administered by parenteral route but recently, also in consideration of deeper knowledges acquired on the pharmacodynamics of the molecule, the drug's administration by the oral route attracts considerable interest.

Particularly, the possibility of devising therapeutic indications in fields such as that of aging, makes up-to-date slow-release, oral administration forms, which are more suited for prolonged treatments, granting a uniform and continuous availability of the active principle.

The CDP-choline derivatives object of the present invention fulfil said requisites.

The used functionalization strategy is based on the binding of CDP-choline to macromolecular matrices by means of biodegradable covalent bonds, i.e. so as to be cleaved by the enzymes and by the chemico-physical conditions existing in the organism, providing a gradual release of the active principle, which is metabolized.

A series of analogues has been synthesized in order to better analyze the structure-function ratio underlying the slow-release mechanism and the structure protection of the active principle, characterizing this class of CDP-choline derivatives.

The insertion of the drug into a macromolecular matrix modifies in fact in a remarkable manner the structural identity of the active principle, which is not recognized by the degradative enzymes.

In the case of oral formulations, the polymer containing CDP-choline acts at the gastro-enteric apparatus level as a reservoir, wherein the molecular structure of the active principle is preserved and from which the CDP-choline release takes place gradually. The drug release, by cleavage of the covalent bonds binding CDP-choline to the polymeric matrix, is due to the enzymes and to the chemico-physical characteristics of the gastro-enteric medium. Once released the drug, the macromolecule acting as a carrier, if not biodegradable, is excreted by the faecal route, being not absorbed at the gastro-enteric level because of its high molecular weight.

For the parenteral formulations the molecular mechanism of the active principle release is similar to that above described for the oral forms. In this case, the characteristics of the carrier polymeric matrix must be so as to allow the elimination by the urinary route or due to its biodegradability or since its molecular weight allows the elimination thereof in the urine through the glomerular barrier.

The functionalization strategy of CDP-choline according to the invention is extremely interesting not only with respect to the previously mentioned pharmacological mechanisms, but also for the easiness of the drug optimization as a function of the chemical nature of the polymer, of its molecular weight, of its cross-linking degree and of the number of covalent bonds with the active principle. The high versatility of the macromolecularization process of CDP-choline is original and constitutes one of the characterizing element of the derivatives object of the present invention.

The functional groups present on CDP-choline, which may be used for the formation of covalent bonds with the macromolecular structure, are the $NH_2$ group in 4 on the aromatic nucleus and the OH groups in 2' and 3' on the ribose. The need of obtaining easily biodegradable bonds limit the synthetic possibilities to the formation of the ester and amide bonds, using polymeric matrices having carboxy groups. Examples of said polymeric matrices include, for instance, polymers such polyacrylic, polymethacrylic, polymaleic acids, polyamino acids (polyglutamates, polyaspartates) optionally copolymerized with polyacrylates, polymethaacrylates and polyacrylamides. A number of synthetic strategies may be followed for the preparation of macromolecular CDP-choline derivatives; some alternative possibilities for the various steps characterising the synthetic scheme are listed hereinafter, without any limiting scope.

(a) Macromolecularization: it can be performed either binding CDP-choline to a preformed polymeric matrix or by polymerization of CDP-choline derivatives acylated with polymerizable carboxy acids in conditions not degrading the active principle.

(b) Activation of the carboxy moiety: the carboxy moiety, in order to give rise to the formation of ester- or amide-type bonds with CDP-choline, asks for a previous activation, for instance as an anhydride, chloride or imidazolide. The activation reaction as chloride or imidazolide is carried out in an anhydrous medium, using the conventional halogenating reagents for the chlorides and carbonyldiimidazole for the imidazolides. The reaction yields are quantitative and the solution of the activated derivative may be directly used to acylate CDP-choline.

(c) Reaction medium: the acylation must be preferably carried out in a non-aqueous medium to obtain high yields. Since CDP-choline, for its ionic character, is insoluble even in very polar solvents such as dimethylformamide, it is necessary to use CDP-choline salts with highly lipophilic counter-ions, such as the tetrahexylammonium ion. Thanks to said expedient, the acylation reaction of the CDP-choline tetrahexylammonium salt may be carried out in homogeneous phase, for instance in anhydrous dimethylformamide, by simply adding the activated derivative of the acid dissolved in the same solvent.

(d) Stoichiometry of the acylation reaction: the acylating reagent is generally used in a stoichiometric excess with respect to CDP-choline. In the case of acylation of the active principle with activated derivatives of polymerizable acids such as acrylic or methacrylic acids, up to 9 equivalents of acid per mole of CDP-choline are used. In the case of acylation of the active principle with polymers bearing activated carboxy groups, placed in repetitive and contiguous manner on the polymeric backbone, as for instance in the case of polyacrylic acid, quantitative yields in the binding process of the active principle require stoichiometrics even of 1:30 as CDP-choline moles: equivalents of acid groups in the polymer. In fact, due to its steric hindrance, a CDP-choline molecule bound to the polymeric matrix, tends to prevent new drug molecules from binding to the contiguous activated acid sites. Once completed the CDP-choline binding reaction, the activating groups present in excess may be removed either by $H_2O$ treatment or by treatment with ethanol, forming ethyl esters. In the former case, a polymer which at physiological pH has a mainly ionic character is obtained, while in the latter case the polymeric matrix turns out to be considerably more hydrophobic.

(e) Reaction kinetics: the acylation reaction runs more rapidly in the presence of catalysts such as pyridine or dimethylaminopyridine. The high temperatures give shorter reaction times but above 70° C. the hydrolysis reaction of CDP-choline at the level of the pyrophosphoric bridge occurs, which is an undesired side-effect; optimal temperatures for a fast acylation process with high yields range from 40° to 60° C. Generally, the acylation reaction of CDP-choline takes place in high yields (>90° C.) and, according to the nature of the acylating reagent and to the reaction times, may involve one, two or all three molecular sites which may be acylated. For instance, using polymeric matrices with activated carboxy groups, such as imidazolides, only the acylation of the $NH_2$ moiety in 4 on the cytosine nucleus is obtained after reaction times from 48 to 96 hours. On the contrary, using as acylating reagents the imidazolides of monomeric polymerizable units, such as acrylic and methacrylic acids, in the same reaction times even the hydroxy moieties of the ribose component are acylated.

(f) Polymerization: this synthetic step is required when the formation of the polymeric skeleton is a step subsequent to that of CDP-choline acylation. This is generally carried out with unsaturated acids, such as acylic or methacrylic acid, whose derivatives with the active principle may be then easily polymerized in the presence of catalysts such as ammonium persulfate in aqueous medium, or 2,2'-azobis(isobutyrronitrile) in organic medium. The acylated derivative of CDP-choline is first purified from the reaction mixture by precipitation with about 3 volumes of a slightly polar organic solvent such as ethyl acetate and tetrahydrofuran. Since the polymerization of said highly hindering acylated CDP-choline derivatives may be prevented by steric factors, it is convenient to add polymerizable units acting as spacing groups, thereby forming a copolymer. In the case of mono- or diacylated CDP-choline derivatives with acrylic acid, good spacing groups may be for instance acrylic acid itself, acrylamide or methacrylic acid. The polymerization reaction in aqueous medium may be carried out, for example, using mono- and diacryloyl-CDP-choline with acrylic acid in a molar ratio of 1:6. The reaction, carried out at room temperature under nitrogen in the presence of ammonium persulfate as a catalyst, is completed in about 12 hours. In this case, a cross-linked macromolecule having molecular weight $>5\times10^3$ and $<15\times10^3$ is obtained.

(g) Purification of the macromolecular CDP-choline derivative: the more effective purification system which may be used is the ultrafiltration, using membranes having appropriate "cut-off". After removal under vacuum of the organic solvents possibly present, the polymer aqueous solution is ultra-filtered, allowing to recover the macromolecular fraction alone, which may be thereafter lyophilized. This kind of process may be easily carried out at production level, using standard, industrial ultrafiltration units. Alternatively, the derivative object of the invention may be precipitated from the aqueous solutions by addition of hydrophilic organic solvents, such as tetrahydrofuran, acetone or butanol.

The previously described synthetic methods allow the preparation of a wide range of polymeric CDP-choline derivatives. Those having high molecular weight, which may be represented by the following formula:

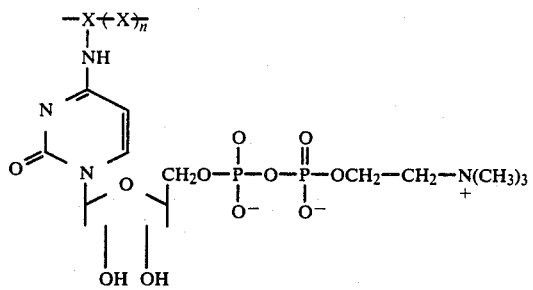

wherein n is an integer from 5 to 30 and X and X' may represent one of the following groups:

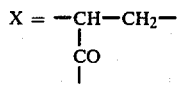   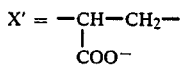

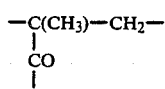   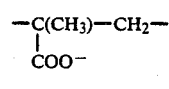

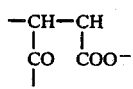   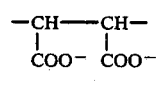

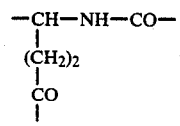   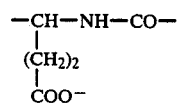

are preferably prepared using high molecular weight polymeric matrices having linear or cross-linked structure, whose carboxy groups, compatibly with the steric hindrances, are linked to the CDP-choline, generally only through one of the three possible acylation sites, preferably the amine moiety in 4 on the cytosine nucleus.

Using hydrosoluble polymeric matrices the CDP-choline derivatives remain soluble, giving viscous solutions. Increases in the cross-linking degree of the polymeric matrix involve a lower solubility and products with a lower amount of CDP-choline for unitary amounts of polymers.

Low molecular weight ($<20\times10^3$) polymeric CDP-choline derivatives of the cross-linked type, which may be schematically represented by the following formula

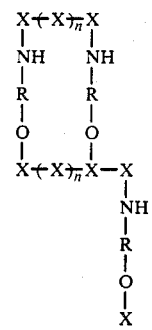

wherein n is an integer from 1 to 10 the —NH—R—O— bridge has the following formula

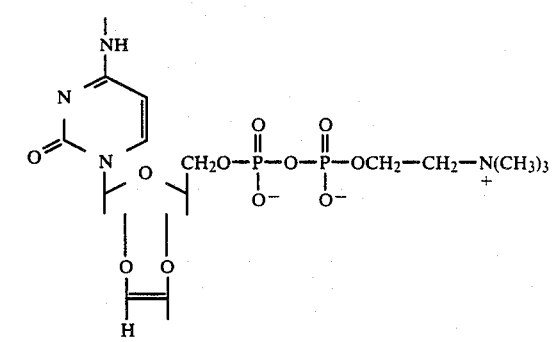

and X and X⁻ may represent one of the following groups

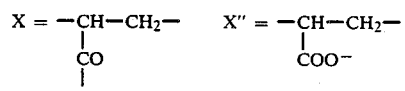

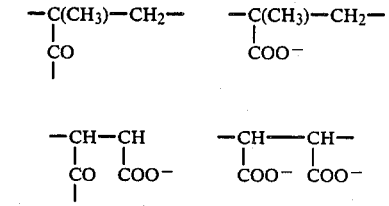

are preferably prepared by copolymerization of mono- or di-acylated CDP-choline derivatives with unsaturated acids or other spacing monomeric units.

The polymeric derivatives of CDP-choline in lyophilized form are white amorphous, indefinitely stable solids. Analogous stability is shown when the products are preserved in aqueous solutions.

As a whole, the methods hereinabove described, for their easiness and low cost, may be easily applied at the industrial level.

The compounds of the invention, due to their biological properties and their behaviour as pro-drugs of the known parent molecule, CDP-choline, may be conveniently used as active principles of pharmaceutical compositions suited for the oral or parenteral administrations, to be used for substantially the same indications of CDP-choline.

Examples of pathologies which may be usefully treated with the compositions of the invention include:

sclerotic vasculopathies mainly interesting the cerebrovascular district;

short- and long-term treatment of cerebrovascular ictuses;

short- and long-term treatment of cerebral ictus consequences;

therapy of the parkinsonian syndrome, in particular in the atherosclerotic form;

antidepressive treatment;

treatment of traumatic cerebral;

prevention and therapy of the ialine membrane disease (IRDS);

therapy of acute and chronic hepatitis (viral hepatitis etc.);

therapy and prevention of the fat liver in alcoholics; coadjuvant therapy in hepatic cirrhosis;

degenerative phenomena due to aging.

The posology of the derivatives of the invention will be determined by their CDP-choline content, and will be so as to allow a daily administration of 100–1,000 mg of CDP-choline.

The compositions object of the invention will be formulated according to conventional methods, using conventional excipients or carriers.

The following Examples, illustrating the preparation and the biological experimentation of a series of polymeric derivatives of CDP-choline, concern only some of the numerous possibilities which may be proposed and do not limit therefore the scope of the invention.

EXAMPLE 1

50 Grams of CDP-choline (0.1 mole) were neutralized with 0.1 mole of tetrahexylammonium hydroxide. After remotion of water by freeze-drying, the salt was dissolved in 2.5 l of anhydrous dimethylformamide (DMF).

3 Equivalents of polyacrylic acid (equivalent weight of the monomeric unit: 70), Mw $2.5 \times 10^5$, dissolved in 2.5 l of anhydrous DMF, were activated as imidazolide by treatment with 3 moles of carbonyl diimidazole. The reaction was carried out at room temperature, and it was complete within about 30 min., as evidenced by the end of $CO_2$ evolution in the solution.

The binding reaction of CDP-choline to the polymeric matrix was effected by admixing the CDP-choline tetrahexylammonium salt solution with polyacrylic acid imidazolide, in the presence of 4-N-dimethylaminopyridine (DMAP) in catalytic amounts (~1 g). The reaction, occurring in homogeneous phase, was left under stirring at 40° C. for 96 hours. After recovering of the solvent by evaporation under vacuum, the dried residue was taken up into 5 l of water and dialyzed against water, using a dialysis membrane having a cut-off of 20,000.

The low molecular weight material was thus separated and the imidazole groups still present on the carboxy residues were removed.

The dialyzed, which could not cross the membrane due to its high molecular weight, was thereafter freeze-dried. Binding of CDP-choline to the polymeric matrix occurred in 90% yields. The obtained product is a white amorphous not hygroscopic solid, which is indefinitely stable at room temperature and, dissolved in water, yields clear and viscous solutions. The so obtained CDP-choline macromolecular derivative has a molecular weight which may be evaluated in $3 \times 10^5$ by means of gel-filtration measurements on Sephadex G-200 and ultrafiltration on Amicon XM-300 membranes with rejection of molecular species $>3 \times 10^5$ CDP-choline macromolecular derivative in aqueous solution shows a maximum at 297 nm, which is typical of CDP-choline N-acylated derivatives, thus evidencing that the active principle, is, under these reaction conditions, bonded to the polymeric matrix by an amide bond at the level of the amino group at −4 on the citosine nucleus. $^1$H-NMR spectrum in $D_2O$ shows, in addition to the broad signals to the polymeric matrix in the interval δ1.1–2.5

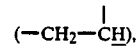

the CDP-choline signals at δ7.4 (H-5), 8.4 (H-6), 6.0 (H-1'), 4.4–4.2 (H-2', 3', 4', 5' and $CH_2$-O-P choline), 3.7 ($CH_2$-N choline), 3.2 ($CH_3$ choline), which loose their multiplicity and broaden, being bonded to the polymeric matrix. Particularly, the $^1$H-NMR data confirm that CDP-choline binding to the polymeric matrix occurs at level of the amino group in 4 of the cytosine nucleus; in fact, the signal of the cytosine proton in 5 falls at lower fields with respect to CDP-choline, analogously to what observed for the other N-acylated derivatives. On the contrary, the protons in 2' and 3' of ribose resonate at the same fields as in CDP-choline, confirming that the sugar hydroxy groups are not esterified.

EXAMPLE 2

The procedure of Example 1 was repeated, but the purification process of macromolecular CDP-choline derivative from the DMF solution was carried out by precipitation with 3 volumes of ethyl acetate. The solid material, washed with 0.5 liters of ethyl acetate, was dissolved in 1 l of $H_2O$ and left under stirring for 24 hours at 40° C., in order to remove the imidazole groups possible present on the carboxy functions.

The solution, concentrated on an ultra-filtration device having membranes with cut-off >100,000 was freeze-dried. The product obtained presents the same characteristics of the product obtained in Example 1.

EXAMPLE 3

The procedure of Example 3 was repeated but when the binding reaction was over, 0.5 l of ethanol were added to the reaction mixture, which was kept for 24 hours at room temperature under stirring. In this way the carboxy residues still activated as imidazolides form ester bonds with the alcohol molecules. After removal of the solvent under vacuum, the dry residue was dyalized against water, using a membrane having a cut-off of about 50,000. In this way, the low molecular weight components were separated, whereas the CDP-choline derivative remained.

The obtained product shows spectroscopical characteristics similar to that of Example 1, with the exclusion of the $^1$H-NMR signals due to the ethyl residues esterifying a part of the acid moieties of the polymeric matrix.

EXAMPLE 4

100 Grams of CDP-choline (0.2 mole) were dissolved in 140 ml of a 40% tetrahexylammonium solution and freeze-dried. The dry CDP-choline tetrahexylammonium salt was then dissolved in 5 l of anhydrous DMF. 1.8 Moles of acrylic acid, dissolved in 2 l of anhydrous DMF, were then reacted with 2.5 moles of carbonyldiimidazole up to ceased $CO_2$ evolution. The CDP-choline tetrahexylammonium salt and 1 g of DMAP in DMF were added to the acrylic acid imidazolide solution, the reaction was kept at room temperature under stirring for 48 hours. The reaction mixture, analyzed on silica thin layer, using as eluent methanol:acetic acid:$H_2O$ (50:15:35 by volume), showed the presence of CDP-choline di-acylated products, with minor amounts of mono- or tri-acylated species.

After evaporation of the mixture up to ¼ of the volume, the CDP-choline acylated species were recovered by precipitation with 3 volumes of ethyl acetate. The product was dried under vacuum in order to remove solvent traces; the yield in acylated derivatives of CDP-choline was about 90%.

100 Grams of the CDP-choline acylated products were dissolved in 6 l of a 100 mM ammonium formiate buffer, adding 0.5 kg of acrylic acid and 6 ml of tetramethylethylenediamine (TEMED) as a catalyst for the polymerization reaction; the so prepared reaction was kept under nitrogen flow for 30'. The polymerization was carried out under protected atmosphere adding 10 mmoles of ammonium persulfate; the reaction at 30° C. was completed in about 24 hours. The polymerization product was purified by ultrafiltration, using a membrane having a cut-off higher than $5 \times 10^3$. The spectroscopical characteristics of the product were analogous to those described in Example 1, the molecular weight, evaluated by membrane filtration, was ranging from $5 \times 10^3$ and $20 \times 10^3$. The yield in the polymerization process was higher than 90%.

EXAMPLE 5

100 Mg of (5-$^3$H; Met-$^{14}$C)CDP-choline (1 mCi of $^3$H and 0.5 mCi of $^{14}$C) tetrahexylammonium salt, dissolved in 8 ml of anhydrous DMF, were reacted with 4 moles of polyacrylic acid imidazolide (Mw $2.5 \times 10^5$), in the presence of 5 mg of DMAP as a catalyst. The reaction was carried out under the conditions of Example 1 and the labelled macromolecular CDP-choline derivative was purified by ultrafiltration on membranes having cut-off of $5 \times 10^4$.

40 Rats (mean body weight 200 g) were orally administered by gastric tube with a dose of the labelled product corresponding to 2 mg of active principle (20 mCi of $^3$H and 10 mCi of $^{14}$C). The animals (10 per group) were sacrificed at 2, 8, 24 and 48 hours. The plasma, stomach, small intestine, large bowel, the gastric and intestinal content, liver, kidneys, feces and urine were removed from the animals and rapidly freezed. The radioactivity level was determined on the biological specimens. The pharmacokinetic pattern showed that CDP-choline was gradually released from the polymeric matrix, essentially at level of the small intestine, where the drug was effectively absorbed. After 8 hours, 80% of the radioactivity in the small intestine content was due to CDP-choline still bound to the polymeric matrix. The distribution pattern of the radioactivity in the organism was comparable to what noticed in the case of administration of doubly-labelled CDP-choline by the oral route, with the difference that in the case of the macromolecular CDP-choline derivative the radioactivity levels were more prolonged in time. The faecal and urinary excretion of radioactivity were extremely poor.

What is claimed is:

1. Macromolecular CDP-choline derivatives wherein CDP-choline is covalently bonded to a polymeric matrix containing carboxy groups, by means of biodegradable amide bonds involving said carboxy groups and the $NH_2$ group in 4 on the aromatic nucleus of the CDP-choline and/or by means of biodegradable ester bonds between said carboxy groups and the OH groups in 2' and 3' of ribose.

2. Derivatives according to claim 1, wherein the polymeric matrix is selected from the group consisting of polyacrylic acids, polymethacrylic, polymaleic, polyaminoacids, or copolymers of polymerizable acids with acrylic acids or acrylamide.

3. Derivatives according to claim 1 or 2, wherein CDP-choline is bound to the polycarboxylic polymeric matrix through an amide bond between the carboxy groups of said polymeric matrix and the $NH_2$ group in 4 of CDP-choline.

4. Derivatives according to claim 1 or 2, wherein CDP-choline is bound to a cross-linked polymeric matrix through amide bonds between the carboxy groups of the polymeric matrix and the $NH_2$ group in 4 CDP-choline and through ester bonds between said carboxy groups and one of the OH groups in position 2' or 3' of ribose.

5. Derivatives according to claim 1 or 2, wherein the carboxy groups of the polymeric matrix not involved in covalent bonds with CDP-choline, are esterified with a lower alcohol.

6. A process for the preparation of derivatives of claim 1, characterized in that a CDP-choline salt with a lipophilic cation is reacted with polymers containing activated carboxy groups, in anhydrous organic solvents and that the reaction mixture is treated with water or lower alcohols.

7. A process according to claim 6, characterized in that a long-chain quaternary ammonium group, preferably tetrahexylammonium, is used as lipophilic cation, and that the carboxy groups are activated as chlorides, anhydrides or imidazolides.

8. Pharmaceutical compositions suited to the oral or parenteral administrations containing as active principles a derivative of claim 1 or 2 in admixture with conventional carriers and excipients.

9. A process for the preparation of a derivative of claim 4, characterized in that an unsaturated polymerizable acid is reacted with a salt of CDP-choline in an anhydrous organic solvent to form a lipophilic salt of a N- and/or O-acylated CDP-choline monomeric product, and the lipophilic salt is then polymerized with an unsaturated polymerizable acid to form said derivative.

10. A process according to claim 9, characterized in that said unsaturated polymerizable acid is selected from the group consisting of polymers of acrylic, methacrylic, and maleic acids and that the polymerization is carried out by radical catalysis.

* * * * *